United States Patent [19]

Chang et al.

[11] Patent Number: 5,596,014
[45] Date of Patent: Jan. 21, 1997

[54] HYDROXYMETHYL-POLYTHIOPHENE DERIVATIVES

[75] Inventors: Ching-Te Chang; Rong-Tsun Wu, both of Taipei, Taiwan

[73] Assignee: Industrial Technology Research Institute, Taiwan

[21] Appl. No.: 461,176

[22] Filed: Jun. 5, 1995

Related U.S. Application Data

[63] Continuation-in-part of Ser. No. 123,432, Sep. 16, 1993, abandoned, which is a continuation-in-part of Ser. No. 71,695, Jun. 4, 1993, Pat. No. 5,508,440.

[51] Int. Cl.$^6$ .......................... A61K 31/38; C07D 409/14
[52] U.S. Cl. .................................. 514/444; 549/59
[58] Field of Search ..................... 549/59, 414; 514/444, 514/460

[56] References Cited

U.S. PATENT DOCUMENTS 5,045,563  9/1991  Morand et al. ........................... 549/59

OTHER PUBLICATIONS

Marles et al (II), "Structure–Activity Studies of Photoactivated Antiviral and Cytotoxic Tricyclic Thiophenes", Photochemistry & Photobiology, vol. 56, No. 4, 1992.

Matsomoto, Y., et al., Kogyo Kagaku Zasshi, (Japan) 62: 1559 (1959).

Winter, C. et al., Biol. Med., 111: 544 (1962).

Roszkowski, A., et al., J. Pharmacol. Exp. Ther., 179: 114 (1971).

Kagan, J., Prog. Chem. Org. National Prod., 56: 88–169 (1991).

Rossi, R. et al., Societa Chimica Italiana, 120: 7930–803 (1990).

*Primary Examiner*—Richard L. Raymond
*Assistant Examiner*—Deborah Lambkin
*Attorney, Agent, or Firm*—Fish & Richardson P.C.

[57] ABSTRACT

A pharmaceutical composition containing a compound and an excipient, the compound having the formula:

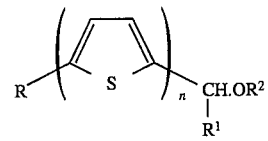

in which n is 2, 3 or 4; R is H, $-CH(R^1) \cdot OR^2$, $-CH(O-Z)_2$, or $-COR^3$; $R^1$ is H, $C_{1-6}$ alkyl, $C_{2-6}$ alkenyl, OH, $C_{1-6}$ hydroxyalkyl, or COOH; $R^2$ is H, $C_{1-6}$ alkyl, $C_{2-6}$ alkenyl, tetrahydropyranyl, phenyl, benzoyl, $C_{1-6}$ acyl, tosyl, or $-CO-Y-COOH$; and $R^3$ is H, $C_{1-6}$ alkyl, $C_{2-6}$ alkenyl, OH, $C_{1-6}$ hydroxyalkyl, or COOH; wherein Z is $C_{1-6}$ alkyl, $C_{2-6}$ alkenyl, or $C_{1-6}$ acyl; and Y is $C_{1-6}$ alkylidene, $C_{2-6}$ alkylidene, phenylene, or deleted; or an ester or a salt thereof.

22 Claims, No Drawings

HYDROXYMETHYL-POLYTHIOPHENE DERIVATIVES

CROSS REFERENCE TO RELATED APPLICATION

This is a file wrapper continuation-in-part of application of Ser. No. 08/123,432, filed Sep. 16, 1993, now abandoned, which is a continuation-in-part of U.S. patent application Ser. No. 08/071,695, filed Jun. 4, 1993 U.S. Pat. No. 5,508,440, which is hereby incorporated by reference.

BACKGROUND OF THE INVENTION

This invention relates to hydroxymethylpolythiophene derivatives and their medical use.

Our chemical and pharmacological studies on the extract of the Compositae Chinese herbs demonstrate that their unique chemical components, hydroxymethylpolythiophene derivatives, possess useful biological activities.

No pharmacological activities of hydroxymethylpolythiophene or derivatives thereof have hitherto been reported.

SUMMARY OF THE INVENTION

The present invention relates to a pharmaceutical composition which comprises an excipient and a compound of the following formula:

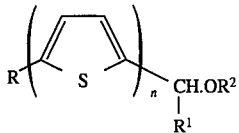

(1)

in which n is 2, 3 or 4; R is H, —CH($R^1$)•$OR^2$, —CH(O—Z)$_2$, or —$COR^3$; $R^1$ is H, $C_{1-6}$ alkyl, $C_{2-6}$ alkenyl, OH, $C_{1-6}$ hydroxyalkyl, or COOH; $R^2$ is H, $C_{1-6}$ alkyl, $C_{2-6}$ alkenyl, tetrahydropyranyl, phenyl, benzoyl, $C_{1-6}$ acyl, tosyl, or —CO—Y—COOH; and $R^3$ is H, $C_{1-6}$ alkyl, $C_{2-6}$ alkenyl, OH, $C_{1-6}$ hydroxyalkyl, or COOH; wherein Z is $C_{1-6}$ alkyl, $C_{2-6}$ alkenyl, or $C_{1-6}$ acyl; and Y is $C_{1-6}$ alkylidene, $C_{2-6}$ alkenylidene, phenylene, or deleted; or an ester or a salt thereof.

Preferably, n is 2 or 3; $R^1$ is H, $C_{1-6}$ alkyl, OH, hydroxymethyl, or COOH; $R^2$ is H, $C_{1-6}$ alkyl, tetrahydropyranyl, benzoyl, $C_{1-6}$ acyl, tosyl, or —CO—Y—COOH; and $R^3$ is H; Z is $C_{1-6}$ alkyl; and Y is $C_{1-6}$ alkylidene or deleted. Also preferred are the compounds in which R is H, $R^1$ is $C_{1-6}$ alkyl and $R^2$ is H, $C_{1-6}$ alkyl, —CO—Y—COOH where Y is —$CH_2CH_2$—, or tosyl. It is particularly preferred that R be H, —CH($R^1$)•$OR^2$, or —$COR^3$, $R^1$ be H and $R^2$ be H, $C_{1-6}$ alkyl, tosyl, or —CO—Y—COOH. Various exemplary compounds within the scope of this invention are shown in Table 1 and Table 2 below.

$C_{1-6}$ hydroxyalkyl refers to a $C_{1-6}$ alkyl group which is substituted with a hydroxyl functionality, e.g., —$CH_2CH_2OH$. The term "alkyl" or "alkenyl," as well as the alkyl/alkenyl moiety of a substituted or divalent alkyl/alkenyl group (e.g., hydroxyalkyl or alkenylidene), refers to both straight and branched carbon skeletons.

The term "phenylene" refers to p-, o- or m-phenylene. As an example, p-phenylene has the structure of

The term "alkylidene" refers to a divalent radical which has two hydrogens fewer than alkane. Examples of $C_{1-6}$ alkylidene include, but are not limited to, $CH_3$—$CH_2$═ and —$CH_2$—$CH_2$—. Similarly, examples of $C_{1-6}$ alkenylidene include, but are not limited to, —CH═CH— and —$CH_2$CH═$CHCH_2$—.

One use of the above-described pharmaceutical composition, among others, is to modulate immune responses, which refers to increase or decrease immune responses, e.g., boost the immune system as demonstrated by proliferation of cells such as macrophages or T lymphocytes. The amount of the compound in a pharmaceutical composition of the present invention varies depending upon factors such as the seriousness of the dysfunction, the manner of administration, the age and the body weight of the subject and the condition of the subject to be treated, and ultimately will be decided by the attending physician or veterinarian. Such amount of the active compound as determined by the attending physician or veterinarian is referred to herein as an "effective amount."

The formulations may conveniently be presented in unit dosage form and may be prepared by any of the methods well known in the art of pharmacy. All methods include the step of bringing the active compound(s) into association with an excipient which constitutes one or more accessory ingredients. In general, the formulations for tablets or powders are prepared by uniformly and intimately blending the active compound with a finely divided solid excipient, and then, if necessary as in the case of tablets, forming the product into the desired shape and size. For apparent reasons, an ester or a salt of a compound of formula (1) which can be used to practice the present invention refers to a pharmaceutically acceptable form.

Other features and advantages of the present invention will be apparent from the following description of the preferred embodiments, and also from the appending claims.

DESCRIPTION OF THE PREFERRED EMBODIMENTS

The pharmaceutical composition of this invention is capable of treating certain diseases or disorders in a subject (i.e., a mammal, such as a human patient).

As an example, it can modulate immune responses via stimulation of the proliferation of both macrophages and T lymphocytes. Macrophages, an important class of immune system cells, are present in most organs in the body. In addition to engulfing and degrading foreign substances, they are also capable of secreting a large number of diverse products, such as interleukin-1 and tumor necrosis factor, which play important roles in various cellular events ranging from proliferation/differentiation of lymphocytes, inflammation to metabolism. On the other hand, T lymphocytes, which make up the majority of lymphocytes in both the peripheral lymphoid tissues and the lymph nodes, show very high specificity of recognizing one particular antigen. Lymphokines released by T lymphocytes, e.g., interleukin-2 and interferons, play critical roles in activation and proliferation of other immune system cells for generating immune responses against viruses, tumors and the like.

Thus, the pharmaceutical composition of this invention, which is capable of stimulating the proliferation of immune system cells such as macrophages and T lymphocytes, can be used as immune response-modulating agents, particularly as therapeutics in the treatment of diseases relating to acute or chronic immune dysfunctions. Examples of such immunodeficiency diseases include, but are not limited to, acquired immunodeficiency symdrome (AIDS), severe combined immunodeficiency (e.g., reticular dysgenesis, and pure T-cell, or combined T- and B-cell, subacute immunodeficiency diseases), purine nucleoside phosphorylase deficiency, thymic hypoplasia (DiGeorge syndrome), immunodeficiency with thymoma, ataxia-telangiectasia, chronic mucocutaneous candidiasis, intestinal lymphangiectasia. Additional applications are in the prevention of AIDS in patients who are HIV positive, but in the earlier stages of illness as evidenced by the signs and symptoms of AIDS related complex (ARC).

Without further elaboration, it is believed that one skilled in the art can, based on the description herein, utilize the present invention to its fullest extent. The following specific embodiments are, therefore, to be construed as merely illustrative, and not limitative of the remainder of the disclosure in any way whatsoever.

CHEMICAL SYNTHESIS

EXAMPLE 1

Synthesis of 5,5'-dihydroxymethyl bithiophene (a) 5-hydroxymethyl-5'-formyl bithiophene (0.2 g) was dissolved in ethanol (50 ml). $NaBH_4$ (0.1 g) was added at room temperature, and stirred for 1 hour. The solution was monitored by thin layer chromatography to determine whether the reaction was completed. $H_2O$ (50 ml) was added and the ethanol was removed under reduced pressure. After filtration, the solid product was recrystallized. The yield was almost quantitative and the melting point of the product was 158°–160° C.

Data of spectra:

$^1H$ NMR ($D^6$-acetone) 7.03–6.87 (m, 4H, protons of thiophene) 4.73 (s, 4H, —$CH_2OH$)

IR (KBr) $cm^{-1}$ 3500–3300 (OH) 3050 2900, 2850 1453, 1415, 1360, 1230, 1200, 1175 1055, 1025, 1002 880, 870, 795

Mass spectrum, m/e (relative intensity) 226 ($M^+$, 100), 209 ($M^+$-OH, 73)

(b) 5-hydroxymethyl-5'-formyl bithiophene (0.6 g) was dissolved in tetrahydrofuran ("THF") (30 ml), $NaBH_4$ (0.16 g) was added, and the solution was stirred for 2 hours at room temperature. THF was removed under reduced pressure. The white solid obtained was washed with water and dried under reducing pressure. The yield was quantitative. The melting point of the product was 155°–156° C.

(c) 5-hydroxymethyl-5'-formyl bithiophene (0.5 g) was reduced in ethanol (75 ml) with $NaBH_4$ (0.3 g). The mixture was stirred for 3 hours at room temperature. The solution was concentrated and n-hexane was added to crystallize the white-powdered product. The crystal was filtered and washed with water. The crystal was dried by reducing the pressure and the yield was quantitative. The melting point of the product was 155°–156° C.

(d) 2-hydroxymethyl-5-iodothiophene was refluxed with Cu powder in dimethyl formamide ("DMF"). This Ullmann condensation also yielded a very low amount of 2,5-dihydroxymethyl bithiophene.

(e) The Ullmann condensation of 2-acetoxymethyl gave 5,5'-diacetoxymethylbithiophene. 5,5'-dihydroxymethyl bithiophene was obtained by alkaline hydrolysis and refined by column chromatography. The yield was about 20%.

EXAMPLE 2

Synthesis of 5,5'-diacetoxymethyl bithiophene 5,5'-dihydroxymethyl bithiophene (0.23 g), pyridine (1.2 ml) and acetic anhydride (0.3 ml) were mixed, stirred and kept overnight. Then the mixture was extracted with ethylacetate. The pyridine and acetic acid were removed by washing with weak base and weak acid, respectively. Silica gel powder was added into the ethyl acetate solution and the solvent was removed under reduced pressure. Coated silica gel powder was added to the silica gel column and chromatographed. The eluant was ethyl acetate/n-hexane (7/3). The white crystal thus obtained was further recrystallized with ethyl acetate/n-hexane mixture. The melting point of the product was 60° C.

Data of spectra:

IR $cm^{-1}$ 1725 (C=O)

Mass spectrum, m/e (relative intensity) 310 ($M^+$, 37) 251 ($M^+$-$CH_3CO_2$, 100) 192 ($M^+$-2 $CH_3CO_2$, 34)

EXAMPLE 3

Synthesis of 5-hydroxymethyl-5'-formyl bithiophene

Phosphorus oxychloride ("$POCl_3$") (1 ml) was added into DMF (20 ml) slowly under nitrogen gas atmosphere in ice bath and stirred for 1 hour. The DMF solution (5 ml) of 5-hydroxymethyl bithiophene (0.5 g) was dropped in slowly. The mixture was stirred for half an hour at room temperature, then the temperature was raised to 50° C. and was further stirred for 3 hours. The reaction solution was poured into potassium carbonate ice water solution. Then the solution was extracted with 100 ml of ethyl acetate. The extract was washed with water and dried over anhydrous magnesium sulfate. The solvent was removed under reduced pressure. The residual solid was purified by column chromatography. The eluant was ethyl acetate/n-hexane (3/7). The slightly yellowish product was recrystallized with ethyl acetate/n-hexane mixture. The melting point of the product was 123°–124° C. The yield was 85%.

Data of Spectra:

$^1H$ NMR 400 MHz ($CDCl_3$), δ value 9.91 (s, 1H, —CHO) 7.73–7.02 (m, 4H, protons of thiophene) 4.91–4.90 (d, 2H, —$CH_2OH$)

IR (KBr) $cm^{31\ 1}$ 3300 (OH) 1640 (C=O) p Mass spectrum, m/e (relative intensity) 224 ($M^+$, 100) 207 ($M^+$-OH, 57) 195 ($M^+$-CHO, 22 )

EXAMPLE 4

Synthesis of 5-acetoxymethyl-5'-formyl bithiophene 5-hydroxymethyl-5'-formyl bithiophene (0.2 g) and pyridine (1 ml) were mixed together. Acetic anhydride (1 ml) was added slowly into the mixture while stirring. Ethylacetate (200 ml) and water (50 ml) were added 2 hours later. The ethyl acetate layer was washed with weak base, weak acid and water. The product was concentrated and purified by column chromatography. The eluant was ethyl acetate/n-hexane (1/9). Slightly yellowish crystal was obtained. The melting point of the crystal was 89°–91° C. The yield was 95%.

Data of Spectra:

$^1H$ NMR 400 MHz ($CDCl_3$), δ value 9.83 (s, 1H, —CHO) 7.64–7.01 (m, 4H, protons of thiophene) 5.20 (s, 2H, —$CH_2OAc$) 2.08 (s, 3H, —$COCH_3$)

IR (KBr) $cm^{-1}$ 1740, 1660 (C=O)

EXAMPLE 5

Synthesis of 5-hydroxmethyl-5"-formyl terthiophene

POCl$_3$ (1 ml) was added to DMF (30 ml) slowly under nitrogen stream in ice bath condition. The solution was stirred for 1 hour and then DMF solution (20 ml) of 5-hydroxymethyl terthiophene (0.5 g) was dropped in slowly. The mixture was stirred for half an hour at room temperature and then the temperature was raised to 60° C. and stirred for further 2 hours. The reaction solution was poured into ice aqueous potassium carbonate solution. The solution was extracted with 300 ml of ethyl acetate and the extract was dehydrated with anhydrous magnesium sulfate. The solvent was removed under reduced pressure and the residual solid was purified by column chromatography. The eluant was ethyl acetate/n-hexane (3/7). The orange colored crystal was obtained and the melting point of the product was 176°–177° C. The yield was 80%.

Data of Spectra:
$^1$H NMR 400 MHz (CDCl$_3$), δ value 9.86 (s, 1H, —CHO) 7.65–6.91 (m, 6H, protons of thiophene) 4.80 (s, 2H, —CH$_2$OH)

IR (KBr) cm$^{-1}$ 3400 (OH) 1660 (C=O)

Mass spectrum, m/e (relative intensity) 306 (M$^+$, 100) 289 (M$^+$-OH, 56)

EXAMPLE 6

Synthesis of 5,5"-dihydroxymethyl terthiophene 5,5'-diformyl terthiophene (1 g) was added into THF (150 ml). The temperature was raised to 50° C. until the solute was completely dissolved, then NaBH$_4$ (0.25 g) was added and stirred for 3 hours at 50° C. The solvent was removed under reduced pressure. Ethylacetate and water were added to dissolve the residual solid. The ethyl acetate layer was washed with water and dried over anhydrous magnesium sulfate. The ethyl acetate layer was filtered and concentrated to obtain slightly yellowish solid (0.95 g). This was recrystallized from alcohol and the melting point of the product was 182°–183° C.

Data of Spectra:
$^1$H NMR 400 MHz (CDCl$_3$), δ value 7.04–6.89 (m, 6H, protons of thiophene) 4.79 (d, 4H, CH$_2$OH) 1.51 (br. s., OH)

Mass spectrum, m/e (relative intensity) 308 (M$^+$, 58) 306 (M$^+$-2H, 100)

EXAMPLE 7

Synthesis of 5-hydroxymethyl-5"-(1-hydroxypropyl)terthiophene 5-hydroxymethyl-5"-formyl terthiophene (0.5 g) was dissolved into anhydrous THF (50 ml). A little excess of calculated amount of 2.0M ethyl magnesium bromide were added to the THF solution under nitrogen atmosphere. The solution was stirred for 3 hours at room temperature. Aqueous ammonium chloride solution was added to hydrolyze the above reaction solution to obtain the product. The product is collected, separated and purified by column chromatography. The eluant was ethyl acetate/n-hexane (3/7) solution and concentrated to obtain orange powdered solid (0.3 g). The melting point was 131°–132° C.

Data of spectra:
$^1$H NMR 400 MHz (CDCl$_3$), δ value 7.03–6.85 (m, 6H, protons of thiophene)

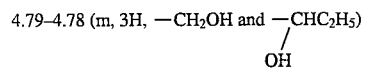

1.91–1.77 (m, 2H, —CH$_2$CH$_3$) 0.99–0.95 (t, 3H, —CH$_3$)
IR (KBr) cm$^{-1}$ 3400 (OH), 2900 (saturated CH)

EXAMPLE 8

Synthesis of 5-succinoyloxymethyl-5'-formyl bithiophene 5-hydroxymethyl-5'-formyl bithiophene (0.63 g), pyridine (10 ml) and succinyl anhydride (0.12 g) were mixed together. The mixture was stirred at 40° C. Thin layer chromatography was applied to monitor the reaction. After the reaction was completed, diluted hydrochloric acid and ethyl acetate were added. The ethyl acetate solution was washed with water to remove pyridine completely. Then the ethyl acetate layer was dehydrated with anhydrous magnesium sulfate and filtered through silica gel layer. After removal of the solvent and the product was recrystallized with ethyl acetate/n-hexane to give a slightly yellowish crystal (0.6 g). The melting point was 127° C.

Data of spectra:
$^1$H NMR 400 MHz (CDCl$_3$), δ value 9.84 (s, 1H, —CHO) 7.65–7.02 (m, 4H, protons of thiophene) 5.25 (s, 2H, —CHO—) 2.72–2.64 (m, 4H, —COCH$_2$CH$_2$CO) 2.40 (br, OH)

IR (KBr) cm$^{-1}$ 3200–2500 (OH) 1730, 1705, 1650 (C=O)

EXAMPLE 9

Synthesis of 5,5'-disuccinoyloxymethyl bithiophene 5,5'-dihydroxymethyl bithiophene (0.5 g), pyridine (10 ml) and succinyl anhydride (2 g) were mixed together. The mixture was stirred at 40° C. Thin layer chromatography was applied to monitor the reaction. After the reaction was completed, ethyl acetate was added to extract the product. The ethyl acetate layer was washed with diluted hydrochloric acid and water in order to remove pyridine completely. The product was filtered through silica gel powder layer and recrystallized with ethyl acetate/n-hexane. White crystal (0.45 g) was obtained. The melting point of the crystal was 137° C.

Data of spectra:
$^1$H NMR 400 MHz (CDCl$_3$), δ value 7.00–6.90 (m, 4H, protons of thiophene) 5.28–5.23 (m, 4H, —CH$_2$O—) 4.78–4.75 (m, 4H, —CH$_2$O) 2.69–2.64 (m, 8H, —CO—CH$_2$CH$_2$—CO—)

IR (KBr) cm$^{-1}$ 3600–2500 (OH) 1718, 1688 (C=O)

EXAMPLE 10

Synthesis of 5-ethoxymethyl terthiophene 5-formyl terthiophene (0.3 g) was dissolved in ethanol (10 ml) by stirring at room temperature. To the solution, 0.04 g of NaBH$_4$ was slowly added. After the solution became clear in about 20 minutes, diluted hydrochloric acid was slowly added until bubbling stopped. The stirring was continued for about 2 hours, followed by chloroform extraction and silica gel column chromatography (eluted by ethyl acetate/n-hexane=1/19). The product was recrystallized with chloroform/ethyl acetate mixture to give a slightly yellowish crystal (melting point 76°–77° C.). The yield was about 41%.

The yield could be increased to 85% or higher by substituting absolute ethanol for alcohol and concentrated hydrochloric acid for diluted hydrochloric acid. More specifically, 5-formyl terthiophene (0.2 g) was first dissolved in absolute ethanol (15 ml) at room temperature. To the solution, 0.03 ml concentrated hydrochloric acid/absolute ethanol mixture (0.3 ml conc. HCl in 10 ml absolute ethanol) was then added. After stirring for 2 hours, 0.8 g sodium bicarbonate ($NaHCO_3$) was added and the stirring was continued for 0.5 hours followed by filtration. The ethanol was removed under reduced pressure. 5-ethoxymethyl terthiophene thus obtained was purified by silica gel chromatography.

Data of spectra:

$^1$H NMR 400 MHz ($CDCl_3$), δ value 7.20–6.87 (m, 7H, protons of thiophene) 4,62 (s, 2H, —$CH_2OC_2H_5$) 3.55 (q, 2H, —$CH_2OCH_2CH_3$) 1.25 (t, 3H, —$OCH_2CH_3$)

IR (KBr) $cm^{-1}$ 3050 (aromatic CH) 2971, 2852 (saturated CH) 1091 (—C—O—)

Mass spectrum, m/e (relative intensity) 306 ($M^+$, 100) 261 ($M^+$-$OC_2H_5$, 33)

EXAMPLE 11

Synthesis of 5-hydroxymethyl tetrathiophene 5-formal tetrathiophene (180 mg or 0.51 mmole) was dissolved in THF (10 ml). $NaBH_4$ (0.1 g) was then added and stirred for 2 hours at room temperature, followed by extraction with $CH_2Cl_2$, washing with water (10 ml×2), dehydration, and filtration through silica gel. The product was recrystallized with THF/n-hexane to give an orange colored solid (150 mg). The melting point was 216° C.

Data of spectra:

IR (KBr) $cm^{-1}$ 3620, 3300 (br) (OH) 3030 (aromatic H) 2925, 2850 (saturated H) 830 (polythiophene)

Mass spectrum, m/e (relative intensity) 360 ($M^+$, 100), 344 (21)

BIOLOGICAL ACTIVITY

Proliferative response of mouse T lymphocytes

The proliferative responses of T lymphocytes colony were also evaluated on the basis of $H^3$-thymidine incorporation. Fresh splenocytes (1×10$^6$ cells/ml) from male C3H/He mice were suspended in a medium containing RPMI 1640 with 0.1 mM nonessential amino acid, 2×10$^{-6}$M 2-mercaptoethanol, 100 units/ml benzylpenicillin, 100 µg/ml streptomycin, 10% heat-inactivated fetal calf serum, and a final concentration of 3 µg/ml of concanavalin a (Sigma). 180 µl aliquots were then added respectively to wells of flat-bottomed microplates (Costar) with or without test compounds, followed by incubation for 3 days at 37° C. in a humidified atmosphere containing 5% $CO_2$. 0.2 µCi of $H^3$-thymidine was subsequently added to each well 18 hour before cell harvest. The incorporated radioactivity was measured using a liquid scintillation counter. These experiments were performed in quadruplicate. (Int. J. Immunopharmacol 12: 777–786 (1990).

TABLE 1

Stimulation of T Lymphocytes by Polythiophene Derivatives

| Test Compound | Doasge (µg/ml) | Activity* |
|---|---|---|
| bithiophene-$CH_2OH$ | 10<br>1<br>0.1<br>0.01 | 0.16<br>2.60<br>1.35<br>1.54 |
| terthiophene-$CH_2OH$ | 10<br>1<br>0.1<br>0.01 | 2,67<br>4.08<br>2.03<br>2.94 |
| $HOH_2C$-terthiophene-$CH_2OH$ | 10<br>1<br>0.1<br>0.01 | 2.24<br>1.95<br>1.88<br>1.62 |
| $HOH_2C$-bithiophene-$CH_2OH$ | 10<br>1<br>0.1<br>0.01 | 1.46<br>1.47<br>1.62<br>1.57 |
| OHC-bithiophene-$CH_2OH$ | 10<br>1<br>0.1<br>0.01 | 0.67<br>1.19<br>1.72<br>2.13 |
| bithiophene-$CH_2$—SA† | 10<br>1<br>0.1<br>0.01 | 1.40<br>1.71<br>1.75<br>1.57 |
| OHC-bithiophene-$CH_2$—SA | 10<br>1<br>0.1<br>0.01 | 1.23<br>1.37<br>0.78<br>0.86 |

TABLE 1-continued

Stimulation of T Lymphocytes by Polythiophene Derivatives

| Test Compound | Dosage (μg/ml) | Activity* |
|---|---|---|
| 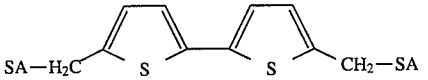 | 10 | 2.39 |
|  | 1 | 1.78 |
|  | 0.1 | 1.10 |
|  | 0.01 | 0.79 |

*expressed as test/blank control of $H^3$-thymidine incorporation
†SA stands for $-OCOCH_2CH_2CO_2H$ As shown in Table 1, all eight test compounds showed their efficacy in stimulating proliferation of T lymphocytes at certain dosages.

Granulocyte-macrophage colony stimulating activity

The proliferative responses of granulocyte-macrophage colony were also evaluated based on $H^3$-thymidine incorporation.

Mouse fibroblast L929 cell conditioned medium was prepared as described by Hines with minor modification. Hines, D., Liquid accumulation and production of colony-stimulating activity by the 266AD cell line derived from mouse's bone marrow, Blood 61:397–402 (1983). L929 cells (1×10⁶) were transferred to a 75 sq. cm² tissue culture flask and cultured for 5 days with 10% FCS at 37° C. in 5% $CO_2$ in air. Confluent cells were fed with fresh medium, and conditioned medium was removed after 24 hours, filtered with a millipore 0.22 membrane, and stored at 20° C. until use.

Male C3H/He mice were killed by cervical dislocation. Femoral bone marrow cells for culture and as a source of granulocyte/macrophage progenitor cells were obtained by flushing the marrow cavity with RPMI 1640 medium using a 26-gauge needle. The cells (4×10⁵/ml) were cultured in a medium containing RPMI 1640 with 5×10⁻⁶M 2-mercaptoethanol, 100 units/ml benzylpenicillin, 100 μg/ml streptomycin, 5% heat-inactivated fetal calf serum, and a final 5% v/v concentration of mouse fibroblast L929 conditioned medium. 180 μl aliquots were then added respectively to wells of flat-bottomed microplates (Costar) with or without a test-sample, and were incubated for 4 days at 37° C. in a humidified atmosphere containing 5% $CO_2$. 0.4 μCi of $H^3$-thymidine was subsequently added to each well 18 hour before cell harvest. The cells were freezed and thawed three times, collected, and washed with normal saline and 5% cold trichloroacetic acid (E. Merk, Darmstadt, West German) in a multiple automated cell harvester. The incorporated radioactivity was measured using a liquid-scintillation counter. All assays were done in quadruplicate.

TABLE 2

Stimulation of Phagophytes by Polythiophene Derivatives

| Test Compound | Dosage (μg/ml) | Activity* |
|---|---|---|
| 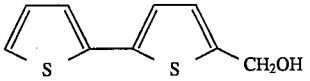 | 10 | 1.38 |
|  | 1 | 1.58 |
|  | 0.1 | 0.87 |
| 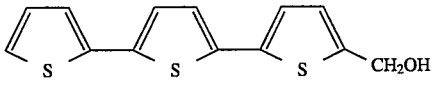 | 10 | 1.34 |
|  | 1 | 1.59 |
|  | 0.1 | 1.34 |
| 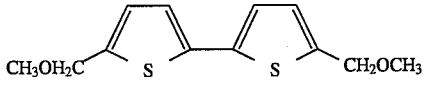 | 10 | 1.96 |
|  | 1 | 2.68 |
|  | 0.1 | 2.10 |
| 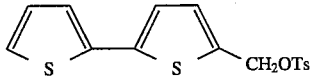 | 10 | 1.92 |
|  | 1 | 1.58 |
|  | 0.1 | 1.17 |

*expressed as test/blank control of $H^3$-thymidine incorporation

As shown in Table 2, all four test compounds showed their efficacy in stimulating proliferation of phagocytes at certain dosages.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions.

We claim:

1. A method of stimulating the proliferation of T lymphocytes or phagocytes in a subject suffering from an immunodeficiency disease, which method comprises the step of administering to the subject a pharmaceutical composition including a compound and an excipient, said compound having the formula:

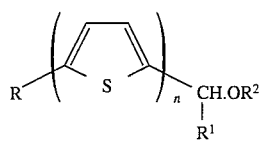

in which n is 2, 3 or 4; R is H, —CH($R^1$)•$OR^2$, —CH(O—Z)$_2$, or —$COR^3$; $R^1$ is H, $C_{1-6}$ alkyl, $C_{2-6}$ alkenyl, OH, $C_{1-6}$ hydroxyalkyl, or COOH; $R^2$ is H, $C_{1-6}$ alkenyl, $C_{2-6}$ alkenyl, tetrahydropyranyl, phenyl, benzoyl, $C_{1-6}$ acyl, tosyl, or —CO—Y—COOH; and $R^3$ is H, $C_{1-6}$ alkyl, $C_{2-6}$ alkenyl, OH, $C_{1-6}$ hydroxyalkyl, or COOH; wherein Z is $C_{1-6}$ alkyl, $C_{2-6}$ alkenyl, or $c_{1-6}$ acyl; and Y is $C_{1-6}$ alkylidene, $C_{2-6}$ alkenylidene, phenylene, or deleted; or an ester or a salt thereof; said composition being administered in an amount effective to stimulate the proliferation of said immune system cells.

2. The method of claim 1, wherein $R^1$ is H, $C_{1-6}$ alkyl, OH, hydroxymethyl, or COOH; $R^2$ is H, $C_{1-6}$ alkyl, tetrahydropyranyl, benzoyl, $C_{1-6}$ acyl, tosyl, or —CO—Y—COOH; and $R^3$ is H; Z is $C_{1-6}$ alkyl; and Y is $C_{1-6}$ alkylidene or deleted.

3. The method of claim 2, wherein n is 2 or 3.
4. The method of claim 3, wherein R is H.
5. The method of claim 4, wherein $R^1$ is H.
6. The method of claim 5, wherein $R^2$ is H or tosyl.
7. The method of claim 5, wherein $R^2$ is —CO—Y—COOH.
8. The method of claim 7, wherein Y is —$CH_2$—$CH_2$—.
9. The method of claim 3, wherein R is —$COR^3$ or —CH($R^1$)•$OR^2$.
10. The method of claim 9, wherein R is —$COR^3$.
11. The method of claim 10, wherein $R^3$ is H.
12. The method of claim 11, wherein $R^1$ is H.
13. The method of claim 12, wherein $R^2$ is H.
14. The method of claim 12, wherein $R^2$ is —CO—Y—COOH.
15. The method of claim 14, wherein Y is —$CH_2$—$CH_2$—.
16. The method of claim 3, wherein R is —CH($R^1$)•$OR^2$.
17. The method of claim 16, wherein $R^1$ is H.
18. The method of claim 17, wherein $R^2$ is H.
19. The method of claim 17, wherein $R^2$ is —$CH_3$.
20. The method of claim 17, wherein $R^2$ is —CO—Y—COOH.
21. The method of claim 20, wherein Y is —$CH_2$—$CH_2$—.
22. The method of claim 1, wherein R is H, $R^1$ is $C_{1-6}$ alkyl and $R^2$ is H, $C_{1-6}$ alkyl, —CO—Y—COOH where Y is —$CH_2CH_2$—, or tosyl.

* * * * *